United States Patent
Iannotta et al.

(10) Patent No.: US 10,689,308 B2
(45) Date of Patent: *Jun. 23, 2020

(54) SOLVENT FOR THIOPHOSPHORIC TRIAMIDE OR DICYANDIAMIDE SOLUTIONS, AND RELATED METHODS

(71) Applicant: RHODIA OPERATIONS, Paris (FR)

(72) Inventors: Leahann Iannotta, Wayne, PA (US); Rajesh Pazhianur, Belle Mead, NJ (US); Samantha Armisen, Villenave d'Ornon (FR); Chloe Moreau, La Plaine Saint Denis (FR)

(73) Assignee: RHODIA OPERATIONS, Paris (FR)

( * ) Notice: Subject to any disclaimer, the term of this patent is extended or adjusted under 35 U.S.C. 154(b) by 105 days.

This patent is subject to a terminal disclaimer.

(21) Appl. No.: 15/515,790

(22) PCT Filed: Sep. 29, 2015

(86) PCT No.: PCT/US2015/052897
§ 371 (c)(1),
(2) Date: Mar. 30, 2017

(87) PCT Pub. No.: WO2016/054012
PCT Pub. Date: Apr. 7, 2016

(65) Prior Publication Data
US 2017/0305807 A1    Oct. 26, 2017

Related U.S. Application Data

(60) Provisional application No. 62/057,698, filed on Sep. 30, 2014, provisional application No. 62/212,880, filed on Sep. 1, 2015.

(51) Int. Cl.
| C05G 3/90 | (2020.01) |
|---|---|
| C07F 9/22 | (2006.01) |
| C07F 9/11 | (2006.01) |
| C05G 5/20 | (2020.01) |
| C05G 5/00 | (2020.01) |
| C05C 1/00 | (2006.01) |
| C05C 3/00 | (2006.01) |
| C05C 9/00 | (2006.01) |
| C07C 279/28 | (2006.01) |

(52) U.S. Cl.
CPC ............. C05G 3/90 (2020.02); C05C 1/00 (2013.01); C05C 3/005 (2013.01); C05C 9/005 (2013.01); C05G 5/20 (2020.02); C05G 5/45 (2020.02); C07C 279/28 (2013.01); C07F 9/11 (2013.01); C07F 9/224 (2013.01)

(58) Field of Classification Search
CPC ...... C05G 3/08; C05G 3/0064; C05G 3/0052; C05C 9/005; C05C 1/00; C05C 3/005; C07F 9/11; C07F 9/224; C07C 279/28
See application file for complete search history.

(56) References Cited

U.S. PATENT DOCUMENTS

| 4,530,714 A | 7/1985 | Koic et al. |
|---|---|---|
| 4,686,790 A | 8/1987 | Lahalih et al. |
| 5,352,265 A | 10/1994 | Weston et al. |
| 5,698,003 A | 12/1997 | Omilinsky et al. |
| 8,163,058 B2 | 4/2012 | Whitehurst et al. |
| 8,617,425 B2 | 12/2013 | Cigler |
| 10,196,322 B2 | 2/2019 | McKnight et al. |
| 10,221,108 B2 | 3/2019 | McKnight et al. |
| 2013/0134806 A1 | 5/2013 | Cho |
| 2013/0145806 A1 | 6/2013 | Iannotta et al. |
| 2014/0060132 A1 † | 3/2014 | Roberts |
| 2014/0090432 A1 † | 4/2014 | McKnight |
| 2014/0174140 A1 * | 6/2014 | Ortiz-Suarez ............ C05G 3/08 71/27 |
| 2015/0143860 A1 * | 5/2015 | McKnight ................ C05G 3/08 71/28 |
| 2015/0299062 A1 † | 10/2015 | McKnight |

FOREIGN PATENT DOCUMENTS

| CN | 101200400 B | 6/2008 |
|---|---|---|
| CN | 103571257 A * | 2/2014 |

* cited by examiner
† cited by third party

Primary Examiner — Jennifer A Smith
(74) Attorney, Agent, or Firm — Vorys, Sater, Seymour and Pease LLP

(57) ABSTRACT

Solvents useful with thiophosphoric triamide urease inhibitors, that provide stable solution of a thiophosphoric triamide, such as for distribution (in low or high concentrations) onto a fertilizer or other liquid or solid material that contains urea.

22 Claims, No Drawings

SOLVENT FOR THIOPHOSPHORIC TRIAMIDE OR DICYANDIAMIDE SOLUTIONS, AND RELATED METHODS

This application is a U.S. national stage entry under 35 U.S.C. § 371 of International Application No. PCT/US2015/052897 filed Sep. 29, 2015, which claims the benefit of U.S. Provisional Patent Application Ser. No. 62/057,698 filed Sep. 30, 2014, and U.S. Provisional Patent Application Ser. No. 62/212,880 filed Sep. 1, 2015, both entitled SOLVENT FOR THIOPHOSPHORIC TRIAMIDE SOLUTIONS, AND RELATED METHODS, the contents of which are incorporated herein by reference.

FIELD OF THE INVENTION

The following description relates to compositions (especially solutions) that contain thiophosphoric triamide and triethyl phosphate as a solvent, dicyandiamide and triethyl phosphate as a solvent, or both thiophosphoric triamide and dicyandiamide with triethyl phosphate as a solvent, the solvent optionally containing one or more co-solvent; compositions made or derived therefrom; and related methods of preparing and using these compositions and derivative compositions.

BACKGROUND

The agricultural industry uses a variety of fertilizers to apply macronutrients to crop plants, either by application to the soil or application to plant leaves. Nitrogen, phosphorus, potassium, calcium, magnesium, and sulfur are six macronutrients commonly applied to agricultural crops or soil. Nitrogen is commonly applied in the form of urea or as an ammonium salt such as ammonium phosphate.

Urea, by some estimates, constitutes forty-six percent of the worldwide consumption of nitrogen in agriculture and is the most widely used nitrogen fertilizer. But after application to soil the urea compound is susceptible to hydrolysis, which converts the urea to gaseous ammonia and carbon dioxide. The reaction is catalysed by the enzyme urease, which is produced by some bacteria and fungi and can be present in soil. The gaseous ammonia will volatilize to the atmosphere resulting in substantial loss of nitrogen from the total amount applied as urea fertilizer to a field.

To prevent the hydrolysis reaction of urea in a urea-based fertilizer after application, a urease inhibitor may be included in or added to the urea-based fertilizer. The urease inhibitor can prevent conversion of the urea by urease to gaseous ammonia, preventing the loss of nitrogen from the fertilizer to the atmosphere. Preventing conversion of the urea to ammonia will increase the amount of urea (and, necessarily, nitrogen) from the fertilizer that remains in the soil for absorption by a crop plant, making the urea available to plants in the soil for an extended time period. Increasing the amount of time that the urea is available to the plant increases the effectiveness of the fertilizer, which improves crop yield and quality.

Among effective urease inhibitors are the thiophosphoric triamide compounds disclosed in the U.S. Pat. No. 4,530,714 (incorporated herein by reference), including alkyl thiophosphoric triamide compounds such as N-alkyl thiophosphoric triamides. The compound N-(n-butyl)thiophosphoric triamide (NBPT) is the most common species of thiophosphoric triamide compounds currently used in commercial agriculture.

Thiophosphoric triamide compounds, including N-(n-butyl)thiophosphoric triamide, can be in the form of a solid, waxy material that decomposes by the action of moisture and elevated temperature. These materials are known to be difficult to process, such as to incorporate the material into a derivative composition such as a urea-based fertilizer. Desirably, to facilitate processing, the thiophosphoric triamide material can be dissolved in a solvent to form a solution that contains the dissolved thiophosphoric triamide. The solution should meet basic practical requirements including: high solubility and stability of the thiophosphoric triamide compound in the solution; resistance of the solution to crystallization at low temperature; suitably low viscosity of a solution for processing; low toxicity; low volatility; low flammability; minimum content of water; and preferably low cost.

Examples of solvents that have been identified as useful for forming a solution of solvent and urease inhibitor (e.g., NBPT) are described in patent documents that include U.S. Pat. Nos. 5,698,003; 8,163,058; 8,617,425; U.S. Patent Application Publication Number 2013/0134806; and U.S. Patent Application Publication Number 2014/0090432; the entireties of these documents being incorporated herein by reference.

Separately or in combination a urease inhibitor, a "nitrification inhibitor" can be added to or applied with a nitrogen-based fertilizer to prevent denitrification loss. An example of a nitrification inhibitor is dicyandiamide (DCD). When applied with a nitrogen-based fertilizer, DCD can help prevent the loss of nitrogen through denitrification and leaching. But physical properties of DCD create challenges to its use by application to crops or soil. Dicyandiamide in a solid form exhibits a very low solubility in water (about 41 grams per liter), making it difficult to directly incorporate into an aqueous end use fertilizer composition. One method of using DCD is in a crystalline form, which can be added directly to an aqueous-based nitrogen fertilizer. However, the low water solubility of DCD makes this technique difficult. Alternately, to bypass a step of soluhilizing DCD, DCD can be added to molten urea and granulated. See, e.g., U.S. Pat. No. 5,352,265. This eliminates the need to dissolve the DCD in a solvent.

The agriculture and agriculture chemical industries continue to search for still more options for solvents useful for dissolving and processing urease inhibitors such as NBPT, and nitrification inhibitors such as DCD, into commercial fertilizer materials and other products.

SUMMARY

Urease inhibitors and nitrification inhibitors are well known in the chemical and agricultural chemical arts, and are described in myriad patent documents including U.S. Pat. No. 4,530,714, the entire contents of that document being incorporated herein by reference. Urease inhibitors are useful in fertilizer products, especially urea-based fertilizers, which may be liquid or solid (e.g., granules). Urease inhibitors may also be useful to prevent nitrogen loss from animal wastes (excrements, manure), which are caused by the enzymatic cleavage of urea present in the wastes, to gaseous ammonia. Similarly, urease inhibitors may be used in spray or other products designed to mask animal urine odor. Nitrification inhibitors are also useful with and may be incorporated into nitrogen-based fertilizers to help prevent the loss of nitrogen through denitrification and leaching (optionally in combination with a urease inhibitor).

To incorporate a urease inhibitor or a nitrification inhibitor into a fertilizer or other useful composition, the urease inhibitor or nitrification inhibitor can preferably be processed by use of a solvent in which the urease inhibitor or nitrification inhibitor will effectively dissolve. According to the present description it has now been discovered that urease inhibitors such as thiophosphoric triamides, especially N-(n-butyl)thiophosphoric triamide, as well as nitrification inhibitors such as dicyandiamide, can be dissolved in solvent that includes triethyl phosphate. The solvent can be entirely (e.g., 100 percent) triethyl phosphate, or may include triethyl phosphate in combination with a major or minor amount of one or more co-solvent such as an alkyl (e.g., ethyl) lactate, dimethyl sulfoxide, triethyl phosphate, N-methyl pyrrolidone, glycol, glycol derivative, propylene glycol, sulfolane, or a combination of two or more of these co-solvents. Other exemplary solvents can include triethyl phosphate in combination with a major or minor amount of a mixture of two or more different co-solvents, such as a mixture of triethyl and ethyl lactate, a mixture of triethyl phosphate and dimethyl sulfoxide, or a mixture of triethyl phosphate, ethyl lactate, and dimethyl sulfoxide.

Examples of useful solutions can contain only the thiophosphoric triamide urease inhibitor compound and solvent, only the dicyandiamide and solvent, or a combination of only the thiophosphoric triamide urease inhibitor and dicyandiamide and solvent, with the solvent containing the triethyl phosphate and optional co-solvent.

Examples of solutions as described herein can include at least one thiophosphoric triamide urease inhibitor (e.g., from about 15 to 50 weight percent of the thiophosphoric triamide urease inhibitor based on total weight of the solution) in solvent (e.g., from 50 to 85 weight percent solvent based on total weight of the solution) that contains triethyl phosphate, and optionally one or more of an alkyl lactate, dimethyl sulfoxide, triethyl phosphate, N-methyl pyrrolidone, glycol, glycol derivative, propylene glycol, sulfolane, or a combination of two or more of these as co-solvent.

Other examples of solutions as described herein can include dicyandiamide (e.g., from about 15 to 50 weight percent of the dicyandiamide based on total weight of the solution) in solvent (e.g., from 50 to 85 weight percent solvent based on total weight of the solution) that contains triethyl phosphate, and optionally one or more of an alkyl lactate, dimethyl sulfoxide, triethyl phosphate, N-methyl pyrrolidone, glycol, glycol derivative, propylene glycol, sulfolane, or a combination of two or more of these as co-solvent.

Any of the useful solutions as described may consist of the thiophosphoric triamide compound (e.g., N-(n-butyl) thiophosphoric triamide) and solvent, meaning that the solution is 100 percent thiophosphoric triamide compound and solvent, the solvent being triethyl phosphate optionally in combination with one or more co-solvent.

Useful solutions as described may consist of the dicyandiamide compound and solvent, meaning that the solution is 100 percent dicyandiamide and solvent, the solvent being triethyl phosphate optionally in combination with one or more co-solvent.

Other useful solutions as described may consist of the thiophosphoric triamide compound (e.g., N-(n-butyl)thiophosphoric triamide), the dicyandiamide compound, and solvent, meaning that the solution is 100 percent thiophosphoric triamide compound (e.g., N-(n-butyl)thiophosphoric triamide), dicyandiamide, and solvent, the solvent being triethyl phosphate optionally in combination with one or more co-solvent.

Other exemplary solutions may consist essentially of the thiophosphoric triamide compound and solvent (including co-solvent), dicyandiamide and solvent (including co-solvent), or the thiophosphoric triamide compound with dicyandiamide and solvent (including co-solvent). A solution that consists essentially of the thiophosphoric triamide compound and solvent, dicyandiamide compound and solvent, or the thiophosphoric triamide compound with dicyandiamide and solvent, is a solution that contains not more than 5 weight percent, e.g., less than 2 weight percent, preferably less than 1, 0.5, or 0.1 weight percent of material or ingredient (e.g., water, adjuvant, impurities) other than the thiophosphoric triamide compound, dicyandiamide, or a mixture thereof, and the solvent (including co-solvent).

Preferred solutions can have a very low water or moisture content, such as below 1 percent, e.g., below 0.5 or 0.1 weight percent moisture based on the weight of the solution.

Preferred solutions are sufficiently stable to allow the solution to be stored over an extended period of time at stable or varied temperature (e.g., at least two weeks at or near room temperature (72 degrees Fahrenheit)) without experiencing separation, crystallization, or chemical breakdown. Preferred solutions can also serve as a vehicle to incorporate the thiophosphoric triamide urease inhibitor, dicyandiamde, or both, into a urea-based solid or liquid fertilizer or other useful derivative composition. The solution can be processed to form any useful derivative, such as a composition useful for coating onto or otherwise incorporating into fertilizer products.

As used herein, the term "alkyl" means a saturated straight chain, branched chain, or cyclic hydrocarbon radical, including but not limited to, methyl, ethyl, n-propyl, iso-propyl, n-butyl, sec-butyl, t-butyl, pentyl, n-hexyl, and cyclohexyl.

In one aspect, the invention relates to a solution that includes: thiophosphoric triamide urease inhibitor, and triethyl phosphate as solvent.

In another aspect, the invention relates to a method of preparing a urea-based fertilizer. The method includes providing a solution as described herein (e.g., including thiophosphoric triamide urease inhibitor, and triethyl phosphate as solvent) and incorporating the solution into the urea-based fertilizer.

In another aspect, the invention relates to a solution that includes: dicyandiamide and triethyl phosphate as solvent.

In another aspect, the invention relates to a method of preparing a urea-based fertilizer. The method includes providing a solution as described herein (e.g., including dicyandiamide and triethyl phosphate as solvent) and incorporating the solution into the urea-based fertilizer.

DETAILED DESCRIPTION

Following is a description of solvents, solvent-containing compositions such as solutions, and agricultural products and derivatives thereof. These compositions and solutions can include urea-based fertilizer compositions that contain a urease inhibitor from the group of thiophosphoric triamide urease inhibitors. The compositions can alternately or additionally contain a nitrification inhibitor such as dicyandiamide (DCD). A composition includes triethyl phosphate as a solvent, either alone or as part of a solvent system containing triethyl phosphate with one or more co-solvent.

The thiophosphoric triamide urease inhibitor may be an alkyl thiophosphoric triamide, e.g., an N-alkyl thiophosphoric triamide, for example N-(n-butyl)-thio-phosphoric triamide, also referred to herein as NBPT. It is understood that the terms thiophosphoric triamide, alkyl thiophosphoric triamide, N-alkyl thiophosphoric triamide, and N-(n-butyl)-thio-phosphoric triamide as used throughout this application refer not only to the specific materials in a pure form, but also to commercial grades of such materials, which may contain up to 50 percent, preferably not more than 20 percent, of impurities, depending on the method of synthesis and purification scheme, if any, used in preparation of the material.

Industrial grade thiophosphoric triamides are often waxy and sticky materials that are difficult to handle and process to derivative products using conventional industrial equipment and methods. Thiophosphoric triamides are also of low solubility in water, in aqueous solutions such as ammonium hydroxide solutions, and in various common organic solvents such as toluene, benzene, hexane, dichloromethane, and others. Lower alcohols are good solvents for the N-alkyl thiophosphoric triamides but are flammable, presenting safety problems. Also, alkyl thiophosphoric triamides are considered to be unstable in many aqueous and non-aqueous solvents.

Dicyandiamide is a known chemical compound, effective as a nitrification inhibitor, and having the formula (1):

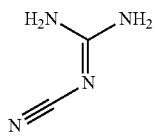

Dicyandiamide, also known as "2-cyanoganidine," can be made by known methods of treating cyanamide with base, and is commercially available. Dicyandiamide can be provided in the form of a concentrated solid ingredient, e.g., a flake, pellet, or granule, that contains a high concentration of the DCD, e.g., at least 50, 75, or 90 weight percent DCD. The dicyandiamide also preferably contains a low amount of moisture, such as less than 5, 2, or 1 percent water based on the total weight of the DCD composition.

According to the present description, triethyl phosphate can be a useful solvent for a nitrification inhibitor such as DCD; for a urease inhibitor such as a thiophosphoric triamide, an alkyl thiophosphoric triamide, a N-alkyl thiophosphoric triamides, or a N-(n-butyl)-thio-phosphoric triamide; or for a combination of the nitrification inhibitor (e.g., DCD) and one or more of these urease inhibitors.

Triethyl phosphate, which is the triester of ethanol and phosphoric acid, can alternately be referred to as phosphoric acid triethyl ester, ethyl phosphate, triethylphosphate, tris(ethyl) phosphate, or triethoxyphosphine oxide. Triethyl phosphate is a colorless liquid at room temperature and has the following chemical formula:

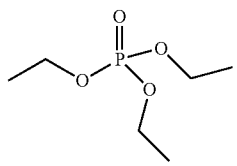

The relative amount of the nitrification inhibitor, the urease inhibitor, or both, in a composition that contains triethyl phosphate as a solvent, can be any amount or amounts useful to allow an effective amount of the nitrification inhibitor, urease inhibitor, or both, to dissolve in the solvent to allow the resultant solution to be processed as desired.

Exemplary amounts of thiophosphoric triamide and triethyl phosphate, as a solvent, a solution that does not contain co-solvent, can be, e.g., from 15 to 50 weight percent thiophosphoric triamide, and from 50 to 80 weight percent triethyl phosphate, for example from 20 to 35 weight percent thiophosphoric triamide and from 65 to 80 weight percent triethyl phosphate. The solution may consist of or may consist essentially of the thiophosphoric triamide and triethyl phosphate.

Exemplary amounts of DCD, with triethyl phosphate as a solvent, in a solution that does not contain co-solvent, can be, e.g., from 15 to 50 weight percent DCD, and from 50 to 85 weight percent triethyl phosphate, for example from 20 to 35 weight percent DCD and from 65 to 80 weight percent triethyl phosphate. The solution may consist of or may consist essentially of the DCD and triethyl phosphate.

Exemplary amounts of DCD and NBPT, with triethyl phosphate as a solvent, in a solution that does not contain co-solvent, can be, e.g., from 15 to 50 weight percent DCD and NBPT, and from 50 to 85 weight percent triethyl phosphate, for example from 20 to 35 weight percent DCD and NBPT and from 65 to 80 weight percent triethyl phosphate. The solution may consist of or may consist essentially of the DCD, NBPT, and triethyl phosphate.

Optionally, the solution may also contain at least one additional solvent (referred to as a "co-solvent"). The amount and type of co-solvent can be as desired, with certain preferred co-solvents including alkyl lactate (e.g., ethyl lactate), dimethyl sulfoxide, triethyl phosphate, N-methyl pyrrolidone, glycols, glycol derivatives such as propylene glycol, sulfolane, and combinations thereof.

The solution can include triethyl phosphate as the only solvent, or may contain a single co-solvent or a mixture of two or more co-solvents. Where a mixture of co-solvents is used, examples of preferred co-solvent mixtures include a mixture of triethyl and alkyl (e.g., ethyl) lactate; a mixture of triethyl phosphate and dimethyl sulfoxide; and a mixture of triethyl phosphate, alkyl (e.g. ethyl) lactate, and dimethyl sulfoxide.

Exemplary amounts of thiophosphoric triamide, triethyl phosphate, and co-solvent (a single co-solvent or a mixture) in a solution that contains co-solvent can be, e.g., from 15 to 50 weight percent thiophosphoric triamide, from 50 to 85 weight percent triethyl phosphate, and up to about 50 weight percent co-solvent, for example from 20 to 30 weight percent thiophosphoric triamide, and from 70 to 80 weight percent triethyl phosphate, and up to about 30, 25, 15, or 10 weight percent co-solvent based on the weight of the solution. The solution may consist of or may consist essentially of the thiophosphoric triamide, the triethyl phosphate, and the co-solvent.

Exemplary amounts of DCD and co-solvent (a single co-solvent or a mixture) in a solution that contains co-solvent can be, e.g., from 15 to 50 weight DCD, from 50 to 85 weight percent triethyl phosphate, and up to about 75 or 80 weight percent co-solvent, for example from 20 to 30 weight percent DCD, and from 70 to 80 weight percent triethyl phosphate, and up to about 80, 75, 70, 60, 50, 30, 25, 15, or 10 weight percent co-solvent based on the weight of the solution. The solution may consist of or may consist essentially of the DCD, the triethyl phosphate, and the co-solvent.

Exemplary amounts of DCD, thiophosphoric triamide, triethyl phosphate, and co-solvent (a single co-solvent or a mixture) in a solution that contains co-solvent can be, e.g., from 15 to 50 weight percent DCD and thiophosphoric triamide, from 50 to 85 weight percent triethyl phosphate, and up to about 75 or 80 weight percent co-solvent, for example from 20 to 30 weight percent DCD and thiophosphoric triamide, and from 70 to 80 weight percent triethyl phosphate, and up to about 80, 75, 70, 60, 50, 30, 25, 15, or 10 weight percent co-solvent based on the weight of the solution. The solution may consist of or may consist essentially of the DCD, thiophosphoric triamide, the triethyl phosphate, and the co-solvent.

The amount of the co-solvent in the solution may depend on the type of co-solvent. Exemplary levels of alkyl (e.g., ethyl) lactate can be up to about 30, e.g., up to about 25 weight percent based on total weight of the solution; exemplary levels of dimethyl sulfoxide can be up to about 80, 75, 70, 50, 25, or 10 weight percent, e.g., up to about 5 weight percent based on total weight of the solution; exemplary levels of a combination of ethyl lactate and dimethyl sulfoxide can be up to about 30, e.g., up to about 25 weight percent of the combination based on total weight of the solution; exemplary levels of N-methyl pyrrolidone can be up to about 10, e.g., up to about 5 weight percent based on total weight of the solution; exemplary levels of a glycol or glycol derivative (e.g., propylene glycol) can be up to about 15, e.g., up to about 10 weight percent based on total weight of the solution; exemplary levels of sulfolane can be up to about 15, e.g., up to about 10 weight percent based on total weight of the solution.

Optionally, though not required, a composition as described may contain other additives or adjuvants such as, at least one dye, at least one surfactant, stabilizer, etc. Exemplary embodiments of the solution do not contain any additional added ingredient or material such as an additive or adjuvant, and can specifically exclude a dye, surfactant, emulsifier, or stabilizer.

Preferred solutions can be long-term storage-stable and capable of being incorporated into a liquid or solid urea-containing fertilizer or other useful derivative composition. Examples of solutions as described can remain stable (e.g., without separation, crystallization, or undue chemical breakdown) over extended periods of time (e.g., 1 week, 2 weeks, 4 weeks) and at a temperature in a range from about 30 degrees F. to about 120 degrees F. Example solutions can remain stable (e.g., without separation, crystallization, or undue chemical breakdown) for at least 1 week, 2 weeks, or 4 weeks when stored at 72 degrees Fahrenheit.

Preferred solutions exhibit flow and viscosity properties that allow processing of the solution to incorporate the solution into a derivative product. Preferred solutions can be processed to impregnate, coat, or otherwise incorporate thiophosphoric triamide urease inhibitor or DCD (or both) into or onto a urea-based solid or liquid fertilizer. This may be accomplished by use of any of a variety of known fertilizer bulk blending, coating, or processing equipment. Preferably incorporation of the solution into a solid fertilizer can result in thorough and consistent impregnation of the solid fertilizer by the solution and the urease inhibitor or DCD (or both). Alternately, preferred solutions can be miscible with a liquid fertilizer, allowing the solution to be uniformly mixed or blended into the liquid fertilizer.

Exemplary fertilizers into which the solution can be incorporated can include urea-based fertilizers such as: urea (46-0-0), urea ammonium nitrate solutions (UAN) (28-32 percent), and urea ammonium sulfate (33-0-0-12S), among others.

Example Solutions:

Following are examples of solutions of NBPT dissolved in solvent that contains triethyl phosphate and optional co-solvent.

| General Formulation | |
|---|---|
| NBPT | 20-50% |
| Triethyl phosphate | 20-75% |
| Other solvents | 0-50% |

| Examples | |
|---|---|
| Component | % w/w |
| NBPT | 26.70% |
| Triethyl phosphate | 73.30% |
|  | 100.00% |
| NBPT | 26.70% |
| Triethyl phosphate | 48.30% |
| Ethyl lactate | 25% |
|  | 100.00% |
| NBPT | 26.70% |
| Triethyl phosphate | 68.30% |
| DMSO | 5.00% |
|  | 100.00% |
| NBPT | 26.70% |
| Triethyl phosphate | 48.30% |
| Ethyl lactate | 20% |
| DMSO | 5% |
|  | 100.00% |
| NBPT | 26.70% |
| Triethyl phosphate | 68.30% |
| N-methyl pyrrolidone | 5% |
|  | 100.00% |
| NBPT | 26.70% |
| Triethyl phosphate | 63.30% |
| Propylene glycol | 10% |
|  | 100.00% |
| NBPT | 26.70% |
| Triethyl phosphate | 63.30% |
| Sulfolane | 10% |
|  | 100.00% |
| DCD | 20% |
| Triethyl phosphate | 10% |
| DMSO | 70% |
| DCD | 20% |
| NBPT | 5% |
| Triethyl phosphate | 10% |
| DMSO | 65% |

The invention claimed is:

1. A solution comprising:
   N-(n-butyl)-thio-phosphoric triamide as a thiophosphoric triamide urease inhibitor, wherein the thiophosphoric triamide is present in the solution in an amount from 20 to 35 weight percent, by weight of the solution, and
   a solvent, wherein all solvent of the solution is triethyl phosphate, wherein the triethyl phosphate is present in the solution in an amount from 65 to 80 weight percent, by weight of the solution,
   wherein the solution has an absence of surfactant.

2. The solution of claim 1, further comprising a dye.

3. The solution of claim 1, further comprising dicyandiamide.

4. A method of preparing a urea-based fertilizer, the method comprising providing a solution of claim 1 and incorporating the solution into the urea-based fertilizer.

5. The method according to claim 4, wherein the urea-based fertilizer comprises solid particles and the method comprises impregnating the solid particles with the solution.

6. A solution comprising:
N-(n-butyl)-thio-phosphoric triamide as a thiophosphoric triamide urease inhibitor, wherein the thiophosphoric triamide is present in the solution in an amount between about 15 and 50 weight percent, by weight of the solution, and
solvent comprising triethyl phosphate, wherein the triethyl phosphate is present in the solution in an amount between about 50 and 85 weight percent, by weight of the solution, and
a co-solvent selected from alkyl lactate, dimethyl sulfoxide, N-methyl pyrrolidone, a glycol, a glycol derivative, propylene glycol, sulfolane, and combinations thereof, wherein the solution has an absence of surfactant.

7. The solution of claim 6, wherein the co-solvent is selected from: dimethyl sulfoxide; and a mixture of ethyl lactate and dimethyl sulfoxide.

8. The solution of claim 6, wherein the thiophosphoric triamide is present in the solution in an amount 20 to 35 weight percent, by weight of the solution,
wherein the triethyl phosphate is present in the solution in an amount from 65 to 80 weight percent, by weight of the solution, and
wherein all solvent of the solution is said triethyl phosphate and said co-solvent, wherein said co-solvent is selected from the group consisting of alkyl lactate, glycol, glycol derivative, propylene glycol and combinations thereof.

9. The solution of claim 6, wherein the co-solvent is present in the solution in an amount up to about 35 weight percent, by weight of the solution.

10. The solution of claim 6, further comprising a dye.

11. A method of preparing a urea-based fertilizer, the method comprising providing a solution of claim 6, and incorporating the solution into the urea-based fertilizer.

12. The method according to claim 11, wherein the urea-based fertilizer comprises solid particles and the method comprises impregnating the solid particles with the solution.

13. The method according to claim 11, wherein the urea-based fertilizer comprises a liquid and the method comprises incorporating the solution uniformly into the liquid.

14. The method according to claim 11, wherein the urea-based fertilizer is selected from the group consisting of: urea (46-0-0), urea ammonium nitrate solutions (28-32 percent), and urea ammonium sulfate (33-0-0-12S).

15. The solution of claim 6, further comprising dicyandiamide.

16. A solution comprising
dicyandiamide, wherein the dicyandiamide is present in an amount from 20 to 30 wt. %, by weight of the solution, and
a solvent comprising triethyl phosphate, wherein the triethyl phosphate is present in an amount from 70 to 80 wt. % of the solution, and
optionally co-solvent selected from alkyl lactate, dimethyl sulfoxide, N-methyl pyrrolidone, a glycol, a glycol derivative, propylene glycol, sulfolane, and combinations thereof, wherein the co-solvent is up to 10 wt. % of the solution.

17. The solution of claim 16, wherein the solvent consists of the triethyl phosphate.

18. The solution as recited at claim 16, wherein the solution comprises 20 to 30 wt. % dicyandiamide, 70 to 80 wt. % triethyl phosphate and up to 10 wt. % co-solvent selected from alkyl lactate, dimethyl sulfoxide, N-methyl pyrrolidone, a glycol, a glycol derivative, propylene glycol, sulfolane, and combinations thereof.

19. The solution of claim 16, consisting of the dicyandiamide, the triethyl phosphate, optionally the co-solvent, and optionally dyes.

20. A solution of consisting essentially of dicyandiamide, triethyl phosphate, and dimethyl sulfoxide, wherein
the dicyandiamide is present in an amount from 15 and 50 wt. %, by weight of the solution, and
the triethyl phosphate is a solvent, and is present in an amount from 50 to 85 wt. % of the solution, and
the dimethyl sulfoxide is a co-solvent and is present in an amount up to 35 wt. % of the solution.

21. A solution consisting essentially of:
N-(n-butyl)-thio-phosphoric triamide as a thiophosphoric triamide urease inhibitor, wherein the N-(n-butyl)-thio-phosphoric triamide is present in the solution in an amount between about 15 and 50 weight percent, by weight of the solution, and
triethyl phosphate as a solvent, wherein the triethyl phosphate is present in the solution in an amount between about 50 and 85 weight percent, by weight of the solution;
optionally a co-solvent selected from the group consisting of alkyl lactate, dimethyl sulfoxide, N-methyl pyrrolidone, a glycol, a glycol derivative, propylene glycol, sulfolane, and combinations thereof;
optionally dicyandiamide; and
optionally dye,
wherein said solution has an absence of surfactant.

22. The solution of claim 21 consisting of:
the N-(n-butyl)-thio-phosphoric triamide present in the solution in the amount between about 15 and 50 weight percent, by weight of the solution, and
the triethyl phosphate present in the solution in an amount between about 50 and 85 weight percent by weight of the solution;
optionally the co-solvent selected from the group consisting of alkyl lactate, dimethyl sulfoxide, N-methyl pyrrolidone, a glycol, a glycol derivative, propylene glycol, sulfolane, and combinations thereof;
optionally dicyandiamide; and
optionally dye.

* * * * *